United States Patent [19]

Kurz

[11] Patent Number: 4,566,342

[45] Date of Patent: Jan. 28, 1986

[54] ISOKINETIC EXTRACTIVE SAMPLING PROBE

[76] Inventor: Jerome L. Kurz, 33 Losrobles Dr., Carmel Valley, Calif. 93924

[21] Appl. No.: 491,881

[22] Filed: May 5, 1983

[51] Int. Cl.⁴ .............................................. G01N 1/20
[52] U.S. Cl. ............................... 73/863.03; 73/863.58
[58] Field of Search ................ 73/204, 863.01, 863.02, 73/863.03, 863.58

[56] References Cited

U.S. PATENT DOCUMENTS

| | | | |
|---|---|---|---|
| 3,261,199 | 7/1966 | Raynor | 73/863.23 |
| 3,866,475 | 2/1975 | Thompson et al. | 73/863.58 |
| 3,965,748 | 6/1976 | Boubel | 73/863.23 |
| 4,317,365 | 3/1982 | Lauterbach | 73/204 |

Primary Examiner—S. Clement Swisher
Attorney, Agent, or Firm—Leonard Bloom

[57] ABSTRACT

A flow-rate proportional (isokinetic) sampling probe provided with two identical axial-flow thermal flow sensors whose outputs are used in a differential manner together with a sampling nozzle flow controller to extract a flow-rate proportioned sample of fluid passing thereby, wherein one flow sensor is used to sense the velocity of the fluid and the second flow sensor is used to sense the velocity of the fluid captured by the sampling nozzle, the area of which is the same as that for the flowing fluid such that the differences between the flow sensor outputs is directly used to control the sample flow rate and maintain an isokinetic condition under a wide range of fluid conditions. Two identical temperature sensors used respectively for the flow sensors to automatically adjust the operating temperature of the thermal sensors as the ambient temperature changes.

16 Claims, 2 Drawing Figures

ISOKINETIC EXTRACTIVE SAMPLING PROBE

BACKGROUND OF THE INVENTION

The instant invention relates generally to fluid sampling devices and more specifically to the problem of taking a representative sample of a fluid stream to obtain information on the constituents of the fluid in the stream.

One well known application is in the field of air pollution sampling wherein a flow proportional or isokinetic sample is required in order to obtain accurate particulate size and concentration. Specifically, this invention relates to the novel use of two nearly identical thermal flow sensors, operated in a differential manner, wherein one sensor is used to sense the velocity of the fluid stream and the second sensor is used to sense the flow-rate of the sampled stream. Since the two sensors are of identical construction, and operated identically under all conditions, the difference in the rate of loss of thermal energy, from the two sensors is used in conjunction with a sensing and control circuit to change the sample flow-rate by means of a pump, valve or other means, and thereby force the velocity of the fluid passing the flow sensing probe to be equal to the velocity of the fluid stream, which is by definition, isokinetic sampling.

The applicant's experience and expertise in the fields of fluid mechanics, aerosal physics, and instrumentation have demonstrated to him that the current state-of-the art in isokinetic sampling is replete with problems and disadvantages. Prior art devices have been used in which independent absolute measurements are made of fluid velocity and the sample flow-rate by means of conventional instruments such a as pitot velocity probe and an orifice type flow meter. With these devices, additional data must be taken on the temperature, pressure, and composition of the fluid stream before isokinetic sampling is accomplished. One of the most apparent difficulties in source or stack sampling is that the velocity sensing probe is exposed to the "wet" fluid stream, whereas the sample flow-rate meter is usually placed outside of the stack and downstream of a filter and a condensing device used to remove water vapor. Hence the flow-rate meter senses the "dry" fluid conditions and numerous calculations and corrections need to be made in order to obtain the corrected readings such that an accurate isokinetic sample is taken. In the situations in which the fluid composition is unknown, the temperature is rapidly changing or the velocity is rapidly changing, the prior art methods are wholly inadequate.

Therefore, there is a strong felt yet unfulfilled need for the device according to the instant application which fully and automatically corrects for all the aforementioned fluid parameters and enables the user to obtain a valid sample in a much more accurate and efficient manner.

The prior art of which applicant is aware that would appear to be germane to the patent process encompasses the following citations:

Nelson, U.S. Pat. No. 3,469,453; Schneider, U.S. Pat. No. 3,643,508; Bellinga, U.S. Pat. No. 3,950,136; McCorkle, U.S. Pat. No. 3,965,747; Werner, U.S. Pat. No. 4,154,088; Wright, et al. U.S. Pat. No. 4,297,871.

The patent to McCorkle is of interest since he teaches the use of a gas sampling system and method therefore in which a vacuum pressure regulator is disposed in a gas sampling train to simplify isokinetic sampling at selected locations of a sampling nozzle in a gas conducting flue. As shown in this patent, a gas sampling apparatus includes a sampling nozzle having interposed therebetween a condenser, a filter, and a control valve which thereafter communicates with the regulator, thus forming the invention.

Similarly, the patent to Werner teaches the use of an apparatus for measuring the particulate matter content of a gas which includes a temperature control device for permitting application to hot gases and cold wet gases. The apparatus includes an exhaust for coupling with a duct through which gas passes, associated filters, heat exchange passages therein, and a conduit for coupling a heat exchange medium to the exhaust tube passage and a controllable heating element for heating the heat exchange medium in the conduit between a source and the exhaust tube in response to readings taken by plural thermometers disposed within the environment. A plurality of other measuring devices including monometers are included which show differences in static pressure between the outer surface of the nozzle and the interior of the nozzle. The remaining references further delineate the state-of-the-art as known to applicant.

The device according to the instant application is easily distinguished from prior art devices in that both the velocity sensor and the flow-rate sensor are exposed to the same fluid conditions and therefore, no additional measurements and corrections are required. The instant device operates in a differential manner, thus eliminating the disadvantages of prior art devices. The instant device also incorporates automatic fluid temperature compensation such that it will operate over a wide range of operating conditions without adjustment or corrections. The instant device is routinely used with conventional sampling systems which incorporate a pump, condenser, filters, etc.

OBJECTS AND SUMMARY OF THE INVENTION

Accordingly, it is a primary object of the present invention to provide a novel flow-rate proportional or isokinetic extractive fluid sampling device which provides an instantaneous and accurate continuous sample from which information concerning the fluid, such as particulates, gas composition, radiation level, etc. is obtained. Using a unique differential technique an accurate isokinetic or flow-rate proportional extractive sample is obtained independently of all variables such as fluid composition, temperature, pressure, fluid velocity and possible contaminations; the present invention eliminating the need for complex measurements and corrections as is necessary in prior art devices.

It is a further object of the present invention to provide a flow-rate proportional or isokinetic extractive fluid sampling device which incorporates two thermal flow sensors both of which are exposed to the flowing fluid, wherein one sensor senses fluid velocity and the other senses the sampled flow-rate which is captured by a sampling nozzle, wherein both flow sensors are aligned parallel with the flow, the velocity sensor being placed in a tubular structure allowing fluid to pass into and through, such structure primarily used to shield the sensor from mechanical abuse and thermal radiation, if present, wherein such structure has a minimal interference with the fluid velocity; the flow sensor being placed in a second tubular structure with a flow nozzle having a certain bend radius such that the fluid may be withdrawn and at the same time providing structural mounting of the flow sensor; both sensor structures being designed so as to present the same configuration to the fluid flow wherein the same velocity is presented to each sensor but the sample fluid is captured isokinetically by the flow sensor inlet sampling nozzle and tubular structure. Each thermal flow sensor is manufactured, mounted and operated such that each flow sensor experiences the same heat loss under the same conditions and therefore, produces the same output signal for the same fluid velocity under all conditions.

It is another object of the present invention to operate each sensor at a constant temperature by means of a constant temperature anemometer circuit in which a fixed resistor is used to set the operating temperatures. The output of each thermal anemometer may be in the form of a voltage, current or wattage or a combination of such outputs. The difference between the output, thus representing the velocity difference between the two sensors used is used as the input to an analog, digital or a combination thereof, control circuit to effect a change in the sampling fluid flow-rate, thus bringing both sensors into balance and achieving the desired isokinetic condition.

It is another object of the present invention to incorporate additional sensors, either within the isokinetic probe structure or externally, to sense the fluid temperature and use this information to automatically adjust the operating temperature using two identical temperature sensors, wherein each of these temperature sensors is incorporated into its respective constant temperature anemometer circuit, thus providing constant temperature operation at any given fluid temperature but causing the operating sensor temperature to change in a proportional manner with changes in the ambient fluid temperature, having the two objectives of maintaining the operating parameters of the control circuit within its operational limits and to effect the temperature compensation of each flow sensor such that the output of each thermal anemometer circuit is capable of precise calibration with respect to the actual valve of the fluid velocity and sample flow-rate. Thus the differential output between the velocity sensor and the sample flow-rate sensor information is used to control the isokinetic sampling process and the actual or absolute output may be used to provide real-time data on the fluid velocity and sample flow-rate during the sampling process.

It is a further object of this invention to provide a dual sensor configuration in which the fluid velocity is directed parallel to the sensors for the purpose of minimizing the impaction of particulate matter on the sensor. The axial sensor design, because of the small frontal area projected towards the fluid flow, exhibits a greatly reduced opportunity to be influenced by particulate build-up. Because of the differential operation of the present invention, however, the effect of particulate or other contamination build-up on the flow sensors does not effect the ability of the present invention to provide an accurate isokinetic sample.

It is yet another object of the present invention to provide a novel flow-rate proportional or isokinetic sampling device which is economical, efficient and lends itself well to mass production techniques.

DESCRIPTION OF THE PREFERRED EMBODIMENT

Figure 2:
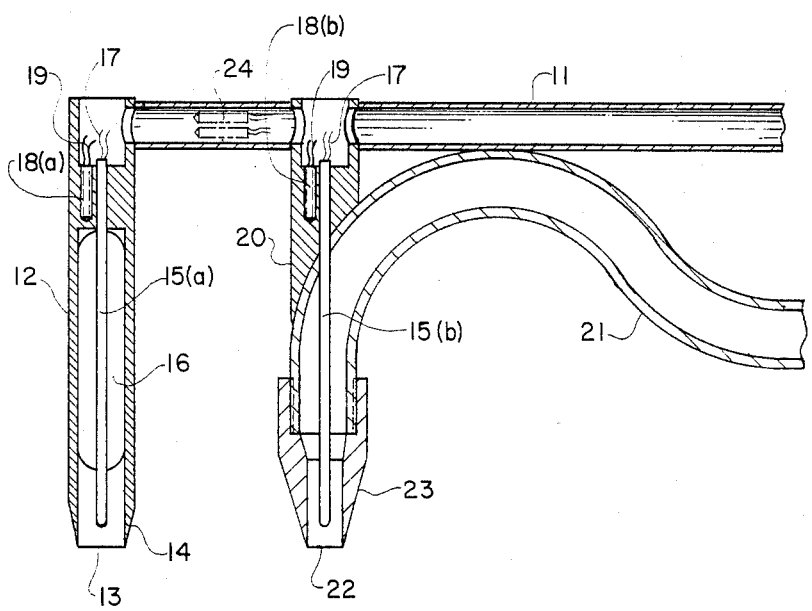
FIG. 2 is a sectional view of that which is shown in FIG. 1.
Figure 3:
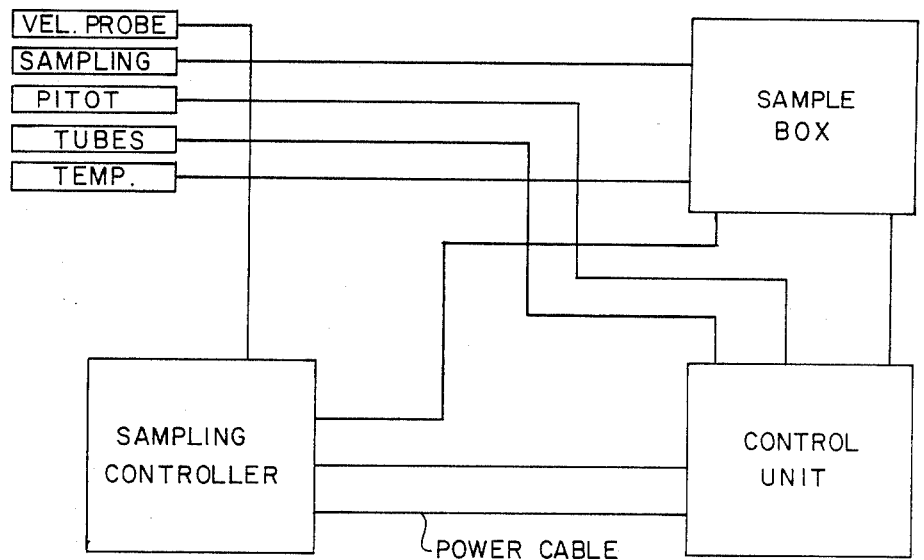

Referring now to the drawings in detail, wherein like reference numerals represent like parts throughout the several figures, reference numeral 10 refers generally to the device according to the instant application. The probe 10 is designed to be installed in a position in the flow of a fluid stream with the fluid passing in the direction of the arrow marked "A", thereby allowing the fluid to pass by the probe 10 with the least-amount of drag or interference. The head of the probe has a tubular conduit 11, which carries the leads from the various sensors to the controlling and instrumentation electronics and control circuitry. The conduit 11 has on an end thereof, a transversely mounted tubular section 12 with a forward opening 13 designed to receive fluid therein. The rim 14 of the opening 13 is beveled to ensure that an accurate and representative sample of fluid is drawn into the opening 13 with minimum disturbance to the fluid stream. The tubular section 12 has a centrally disposed auxiliary mounted thermal flow sensor 15a therein, which is kept at a substantially constant temperature by automatically adjusting the voltage or current fed thereto by means of a thermal anemometer circuit. The tubular section 12 forms a shield around the sensor 15a, the shield having an elongated slot 16, to allow the fluid which passes through the opening 13 to be exhausted through the slot 16. As the fluid passes by the thermal flow sensor, heat from the sensor 15a is dissipated into the fluid according to the flow-rate of the fluid that passes thereby. The faster the flow-rate, the more heat that is dissipated into the fluid and conversely, the slower the flow-rate, the less heat dissipated into the fluid. As abovementioned, the thermal sensor 15a is kept at a substantially constant temperature above the ambient fluid stream temperature by varying the voltage or current fed thereto through electrical leads 17, as shown in FIG. 2. Thus an increased flow of the fluid draws more current or voltage to the sensor 15a in order to keep the sensor at a constant temperature, the converse also being true. Therefore, measurement of the current or voltage output of sensor 15a provides information proportional to the flow-rate of the fluid passing thereby.

A resistance temperature detector 18a is provided in proximity to the thermal sensor 15a to detect changes in the temperature of the ambient fluid passing through the tubular section 12. Thus, as the ambient temperature changes, so does the resistance of the resistance temperature detector 18a, thereby providing a signal for the thermal anemometer circuit to vary the voltage or current fed to the thermal sensor 15a which is kept at a constant temperature above the ambient temperature even as the ambient temperature varies. By way of example only, if the ambient temperature of the fluid is 200° F. then the temperature of the thermal sensor 15a is maintained at 300° F., the ambient temperature being measured by the resistance temperature detector 18a, which controls the voltage or current fed to the thermal sensor 15a. Thus, if the ambient temperature raises from the 200° F. to 250° F., the resistance of the resistance temperature detector 18a changes, thereby indicating that more current or voltage should be fed to the thermal sensor to keep it at a constant differential above the ambient temperatures. Thus, the tubular section 12 along with the sensor 15a and the resistance temperature detector 18a provide a means to measure the actual velocity of the ambient fluid passing thereby. It should be noted that in one embodiment, the aforementioned structures function as a thermal anemometer and measure the unit area mass flow-rate of the fluid stream.

As shown in FIG. 2, a second tubular section 20 is provided along the conduit 11 in proximity to the first tubular section 12 and directly parallel to same. The second tubular section 20 is similarly provided with an axially disposed thermal sensor 15b and a resistance temperature detector 18b, both resistance temperature detectors 18a and 18b having electrical leads 19 to provide a source of current thereto. The second tubular section 20 has joining thereto, along a side thereof, an extractive conduit 21 which has an opening at a forward end thereof, defined by a nozzle 23, the nozzle 23 being removably retained on an end of the extractive conduit 21. The cross sectional area of the opening 22 in the nozzle 23 can be varied according to the flow-rate of the fluid being sampled and the capacity of the pump or other equivalent device extracting the fluid through conduit 21. The fluid conduit 21 functions to extract a sample of the fluid stream therethrough and is used in conjunction with an extractive pump or the like (not shown). The pump draws a sample of the fluid through the fluid nozzle 23 variably, according to the velocity of the fluid passing by the sensor 15a in the first tubular section 12. The pump draws more or less of a sample according to the data obtained from the thermal sensor 15a detailing the velocity of the fluid passing thereby. Thus, as the velocity of the fluid increases, the pump is controlled to extract a greater quantity of fluid from the fluid stream for analysis. Conversely, as the velocity of the fluid decreases, a lesser amount of the fluid is extracted for sampling proportionally. Thus, the nozzle 23 defining the opening 22 can be exchanged according to the size of the opening required, which is determined by the velocity range of the fluid flow being monitored. For example, if the fluid has a high velocity, a nozzle is selected wherein the opening 22 is of a lesser inside diameter than a nozzle selected for a very slight flow-rate. The thermal flow sensor 15b inside the extraction conduit 21 is identical to the thermal sensor 15a inside the tubular section 12 and is similarly controlled through electrical leads 17. The thermal sensor 15b inside the extraction conduit 21 senses the flow of the extractive sample being drawn through the conduit 21, which is varied according to the differential data obtained from the sensors 15a and 15b which monitor the velocity of the flow of the fluid stream and the extractive sample, respectively. Thus, a proportional sample is extracted through the conduit 21 according to the flow-rate of the fluid stream. Thus, the thermal flow sensor 15b in the extraction conduit 21 is made to track the thermal flow sensor 15a in the tubular section 12 by drawing more or less of a sample of the fluid through the conduit 21. For example, if the thermal sensor 15a has an output voltage of X, then the flow of the fluid being drawn through the conduit 21 is varied until the thermal sensor 15b disposed therein will similarly have an output voltage of X, thereby assuring that the sample extracted is representative and proportional to the velocity of the fluid stream at the point of sampling.

Thus, the flow-rate of the extracted sample drawn through the extraction conduit 21 is matched to the flow-rate of the fluid stream monitored by the sensor 15a. Thus, if the sensor 15b is dissipating heat of the sample extraction is increased or decreased accordingly until the sensor 15b is tracking the sensor 15a.

The resistance temperature detectors 18a and 18b, in a preferred embodiment as shown in FIG. 2, are placed proximate to the sensors 15a and 15b, as shown in FIG. 2. However, it should be understood that the placement of the resistance temperature detectors may vary and they may be placed in alternative positions either in a separate structure or such as that shown in FIG. 2, indicated by reference numeral 23, which shows the resistance temperature detectors 18a and 18b placed in the conduit 11 between the tubular section 12 and the second tubular section 20. The resistance temperature detector 18a monitors the temperature of the fluid stream passing by the sensor 15a so that any changes in ambient temperature are immediately monitored and responsed to by varying the voltage or current fed to the sensor 15a so that the sensor 15a remains at a constant temperature above the ambient temperature. Thus, if the ambient temperature is for example 100° F., and the sensor is being run at 100° F. above the ambient temperature, then the sensor 15a will receive enough power to remain at 200° F. If the ambient temperature raises to 300° F., then the sensor temperature is increased automatically to 400° to maintain a constant operating temperature above ambient temperature which is necessary for the sensor 15a to be able to dissipate heat into the fluid stream. Similarly, sensor 15b is kept at the same constant temperature above the ambient temperature utilizing the resistance temperature detector 18b to monitor the temperature of the fluid stream being extracted through the extractive conduit 21. Thus, any differential between voltage or current output of the sensors 15a and 15b indicating that the velocity of the sample being extracted is not the same as the velocity of the fluid stream from which the sample is extracted is used in a control loop to vary the flow-rate of the extracted sample by automatically increasing or decreasing the operating flow-rate of the pump extracting the sample through the extraction conduit 21. Through the use of temperature sensor 18a and 18b the thermal flow sensor 15a and 15b, a temperature compensated constant temperature thermal anemometer circuit (not shown) is used to operate both sensor 15a and 15b which circuit provides the power to maintain the proper operating temperature above the fluid temperature. Similarly, the pump extracting the sample is automatically controlled by a control system (not shown) so that sensor 15b tracks sensor 15a. In this manner, a representative and proportional sample is constantly being extracted through the conduit 21 and isokinetic conditions are maintained.

Through the use of the temperature sensor 18a and 18b, the actual outputs of the circuit driving the fluid velocity sensor 15a and the actual output of the circuit driving the sample flow-rate sensor 15b may be calibrated for fluid temperature variations and exact fluid composition such that both outputs are compensated to be independent of fluid temperature and represent the actual values of the fluid stream velocity and the sample flow-rate for that particular fluid. This automatic temperature compensation feature of the present invention yields both the differential information needed to control the isokinetic sampling process and actual or absolute data on the fluid velocity and the sample flow-rate.

In an alternate embodiment, the thermal flow sensors 15a and 15b may operate at a constant programmable temperature regardless of the ambient temperature and in general, temperature sensors 18a and 18b are not used in the thermal anemometer circuit with thermal flow sensors 15a and 15b, but fixed or variable non-temperature sensitive resistive elements are used, each of which set the operating temperature level of sensors 15a and 15b. This embodiment is useful for situations in which the ambient fluid temperature is relatively constant, or when absolute or actual values of the fluid velocity and sampling flow-rate are not required.

In another alternate embodiment, a computer or microprocessor system may be used to control the operating temperature of flow sensors 15a and 15b based on temperature measurements obtained in detectors 18a and 18b. The same or a similar system may be used to contract the isokinetic sampling process and to obtain actual values of the fluid velocity and sample flow-rate.

Figure 1:
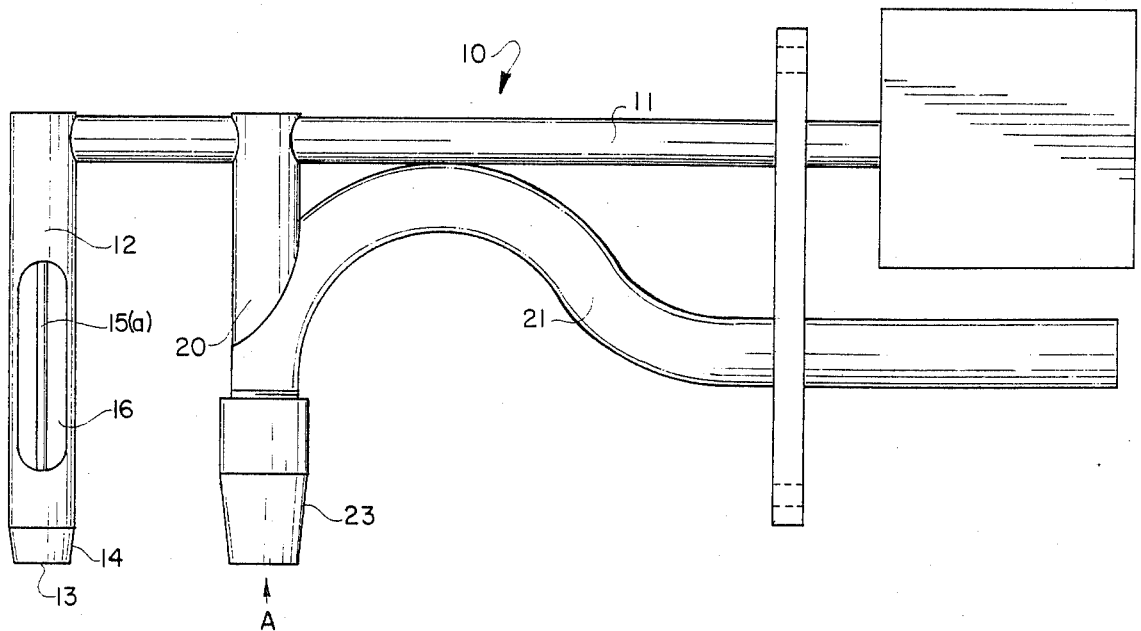
FIG. 1 is a side view of the sampling probe.

In an alternate embodiment, flow sensor 15a and 15b may be placed transverse to the flow direction marked A in FIG. 1 in an alternate structure. This embodiment may or may not include temperature sensors 18a and 18b and their various embodiments referred to previously. Generally, this embodiment is useful for large versions of the present invention wherein large rugged sensors can be placed within the tubular structure 14 and 21 without significantly affecting the precision and accuracy of the present invention.

In a further alternate embodiment, the thermal flow sensors 15a and 15b may be any other type of thermal flow sensor meeting the requirements of the present invention. Similarly, the temperature sensors 18a and 18b may be any type of temperature sensor meeting the requirements of the present invention.

It should be noted that numerous structural modifications and changes may be resorted to without departing from the spirit of the invention.

I claim:

1. An isokinetic extractive sampling probe comprising in combination:
   an elongated probe conduit including,
   a first thermal flow sensor contained within a first tubular section depending from said probe conduit, said first flow sensor directed towards monitoring the velocity of a fluid stream passing thereby,
   a second thermal flow sensor contained within a second tubular section depending from said probe conduit, said second thermal flow sensor directed towards monitoring the velocity of an extractive sample of the fluid being withdrawn from the fluid stream through an extractive conduit,
   said second thermal flow sensor being parallel to the first thermal flow sensor and axially aligned with said second tubular section and
   a first and second temperature sensor to register changes in the ambient temperature of the fluid stream, whereby the differential output between said first thermal flow sensor monitoring the velocity of the fluid stream, and said second thermal flow sensor monitoring the velocity of the extractive sample is used to automatically adjust the flow-rate of the extractive sample being withdrawn through said extractive conduit by pumping means so that velocity of the extractive sample within said extractive conduit is equal to the velocity of the fluid stream, thereby ensuring isokinetic sampling of the fluid streams at the point of measurement.

2. The device of claim 1 wherein said first tubular section is affixed normal to said probe conduit at an end thereof surrounding and shielding said first thermal flow sensor contained therein, and further includes an opening defined by a beveled rim at an opposed end thereof to provide a means of ingress for fluid from the fluid stream to said first flow sensor, the fluid thereafter passing through an egress port defined by an elongated slot in at least one side wall of said first tubular section.

3. The device of claim 2 wherein said second tubular section is truncated on a forward end to intersect with and be affixed to said extractive conduit so that said second flow sensor impinges upon the interior of said extractive conduit in the center thereof, extending through an extractive opening at an end of said extractive conduit, whereby extractive samples withdrawn through said extractive conduit effect said second flow sensor.

4. The device of claim 3 wherein said extractive conduit further includes an arcuate tube with said extractive opening disposed on a forward end thereof, said extractive opening being parallel with said opening in said first tubular section, said extractive opening having removably disposed therearound a tapered nozzle of a known inside diameter, whereby varying the inside diameter of said nozzle allows said sampling probe to function in fluid streams of disparate velocity.

5. The device of claim 4 wherein said first temperature sensor responds to the temperature of the fluid stream and continuously adjusts the operating temperature of said first flow sensor, whereby said first flow sensor operates at a selected temperature above the ambient temperature of the fluid stream and maintains the selected temperature throughout a disparate range of fluid stream conditions.

6. The device of claim 5 wherein second temperature sensor responds to the temperature of the fluid stream and continuously adjusts the operating temperature of said first flow sensor, whereby said second flow sensor operates at a selected temperature above the ambient temperature of the fluid stream and maintains the selected temperature throughout a disparate range of fluid stream conditions.

7. The device of claim 6 wherein the operating temperature of said first flow sensor is selected above the fluid stream temperature and the operating temperature of said second flow sensor is selected above the fluid stream temperature such that an output from said first and second flow sensors is equal under identical velocities in the fluid stream and said extractive conduit.

8. The device of claim 7 wherein the voltage output of said first flow sensor is automatically compared with the voltage output of said second flow sensor, the differential therebetween actuating an extractive pumping means operatively associated with said extraction conduit, whereby the flow-rate of extraction through said extraction conduit is varied accordingly until the voltage output of both sensors is the same which indicates that the velocity of the fluid stream sample being extracted through said extraction conduit is equal to the velocity of the fluid stream, thereby ensuring isokinetic sampling conditions at the point of measurement.

9. The device of claim 8 wherein said first sensor voltage output is calibrated for actual fluid stream velocity.

10. The device of claim 9 wherein said second flow sensor voltage output is calibrated for the actual sample flow-rate for each said sample nozzle.

11. The device of claim 10 wherein both said thermal flow sensors and said temperature sensors are operated such that the electrical current output is measured.

12. The device of claim 11 wherein both said thermal flow sensors and said temperature sensors are operated such that electrical power is measured.

13. The device of claim 12 wherein said first and said second flow sensors are installed within said first and said second tubular sections transversely, whereby said sensors are normal to the flow direction of the fluid stream.

14. The device of claim 13 wherein said first and second sensors operate at a constant temperature, whereby fluid streams of relatively constant ambient temperature can be flow proportionally sampled isokinetically without varying the operating temperature of said sensors.

15. The device of claim 14 wherein several said probes are distributed in a plane normal to the flow direction of the fluid stream, whereby the instantaneous outputs and sample flows are suitably averaged together to obtain a representative isokinetic sample of the entire flow cross section of a fluid conduit that has non-uniform fluid conditions thereacross.

16. A method for ensuring isokinetic sampling of a fluid stream by means of a pair of thermal flow sensors, comprising the steps of
arranging said sensors in a parallel and spaced apart relationship with one another and with said fluid stream, whereby said stream flows parallel to the axial dimensions of said sensors,
monitoring the voltage output required to maintain one of said sensors at a substantially constant temperature, whereby the fluid velocity is monitored by said sensor,
adjusting the voltage output to the second sensor in response to said first monitoring step; and
capturing a sample of said fluid stream with a sampling nozzle of the second sensor.

* * * * *